(12) United States Patent
Lintker

(10) Patent No.: US 12,379,112 B1
(45) Date of Patent: *Aug. 5, 2025

(54) DUCTLESS AIR DISTRIBUTION SYSTEM

(71) Applicant: Johnson Heater Corp., St. Louis, MO (US)

(72) Inventor: Jason Charles Lintker, Webster Groves, MO (US)

(73) Assignee: Johnson Heater Corp., St. Louis, MO (US)

( * ) Notice: Subject to any disclaimer, the term of this patent is extended or adjusted under 35 U.S.C. 154(b) by 387 days.

This patent is subject to a terminal disclaimer.

(21) Appl. No.: 18/129,847

(22) Filed: Apr. 1, 2023

Related U.S. Application Data

(63) Continuation-in-part of application No. 17/150,402, filed on Jan. 15, 2021, now Pat. No. 11,619,419.

(60) Provisional application No. 62/965,474, filed on Jan. 24, 2020.

(51) Int. Cl.
| | |
|---|---|
| *F24F 1/0011* | (2019.01) |
| *A61L 9/20* | (2006.01) |
| *F24F 1/0071* | (2019.01) |
| *F24F 13/10* | (2006.01) |

(52) U.S. Cl.
CPC .............. *F24F 1/0011* (2013.01); *A61L 9/20* (2013.01); *F24F 1/0071* (2019.02); *F24F 13/10* (2013.01); *A61L 2209/16* (2013.01)

(58) Field of Classification Search
CPC ...... F24F 13/1413; F24F 13/222; F24F 13/24; F24F 8/108; F24F 2013/242
See application file for complete search history.

(56) References Cited

U.S. PATENT DOCUMENTS

| | | | |
|---|---|---|---|
| 1,872,599 | A | 2/1928 | Grand |
| 2,555,009 | A | 8/1948 | Romano |
| 2,821,899 | A | 2/1958 | Goettl |
| 2,982,197 | A | 5/1961 | Roberts |
| 2,984,416 | A | 5/1961 | Johnson |
| 3,060,832 | A | 10/1962 | Etal |
| 3,245,224 | A | 4/1966 | Wilkinson |
| 3,252,398 | A | 5/1966 | First |
| 3,552,295 | A | 1/1971 | Armstrong |
| 4,330,047 | A | 5/1982 | Ruspa et al. |
| 4,432,434 | A | 2/1984 | Dean, Jr. |
| 4,621,570 | A | 11/1986 | Bolton et al. |
| 4,635,395 | A | 1/1987 | Movshovitz et al. |
| 4,747,857 | A | 5/1988 | Andrews |

(Continued)

*Primary Examiner* — Allen R. B. Schult
(74) *Attorney, Agent, or Firm* — Carmody MacDonald P.C.; Dennis Jm Donahue, III; Kevin C. Staed

(57) ABSTRACT

The ductless air handling system draws return air from a low level and discharges conditioned supply air at a high level, thereby covering a large area without the need for ductwork. The outlet has a series of upright and lateral vanes with respective adjustable louvers and flaps as well as a curved turning vane along the outlet's back panel and which extends to the top panel. The outlet turns the airflow from a vertical oriented flow to a horizontal oriented flow and directs the airflow outward into the space. The lateral vanes are situated between each upright vane to divide the airflow into a faster-moving upper stream and a slower-moving lower stream that respectively exit through an upper and lower sections of the vent. Further, a germicidal irradiation chamber within the conduit connecting the base to the outlet can disinfect air as it is circulated by the air handler.

20 Claims, 5 Drawing Sheets

(56) References Cited

U.S. PATENT DOCUMENTS

| | | |
|---|---|---|
| 5,046,406 A | 9/1991 | Harris et al. |
| 5,254,034 A | 10/1993 | Roth |
| 5,468,186 A | 11/1995 | Bolton et al. |
| 5,505,379 A | 4/1996 | Wagner |
| 5,531,484 A | 7/1996 | Kawano |
| 5,722,484 A | 3/1998 | Subramanian et al. |
| 5,772,710 A | 6/1998 | Bauer et al. |
| 5,938,527 A | 8/1999 | Oshima et al. |
| 6,606,876 B1 | 8/2003 | Giordano |
| 6,680,028 B1 | 1/2004 | Harris |
| 6,729,843 B1 | 5/2004 | Nichtawitz et al. |
| 7,937,895 B2 | 5/2011 | Janka et al. |
| 8,974,273 B2 | 3/2015 | Uhlenbusch |
| 2008/0017441 A1 | 1/2008 | Takeda et al. |
| 2011/0250830 A1 | 10/2011 | Steinbeiss et al. |
| 2013/0128450 A1 | 5/2013 | Redshaw et al. |
| 2016/0313015 A1 | 10/2016 | Uhlenbusch |

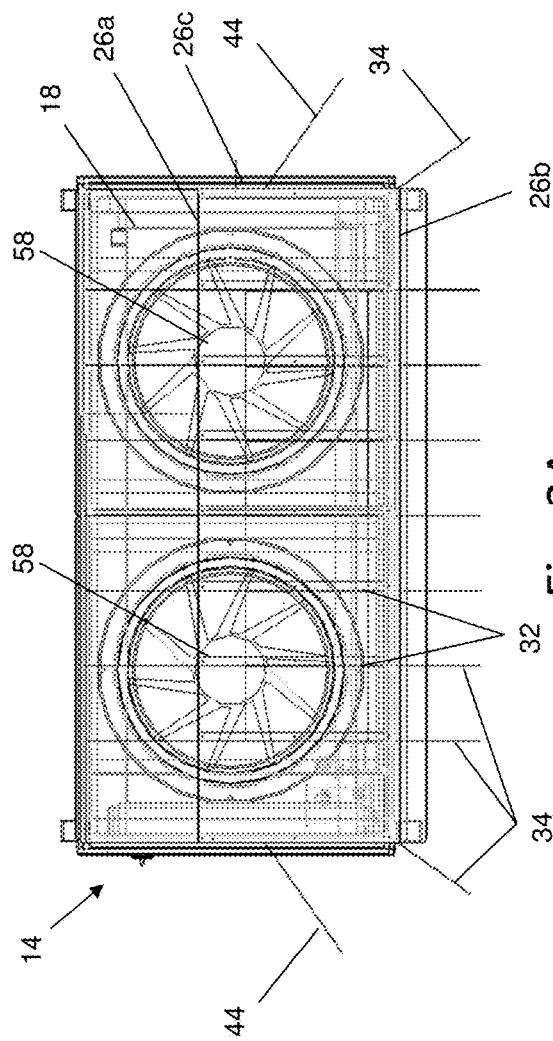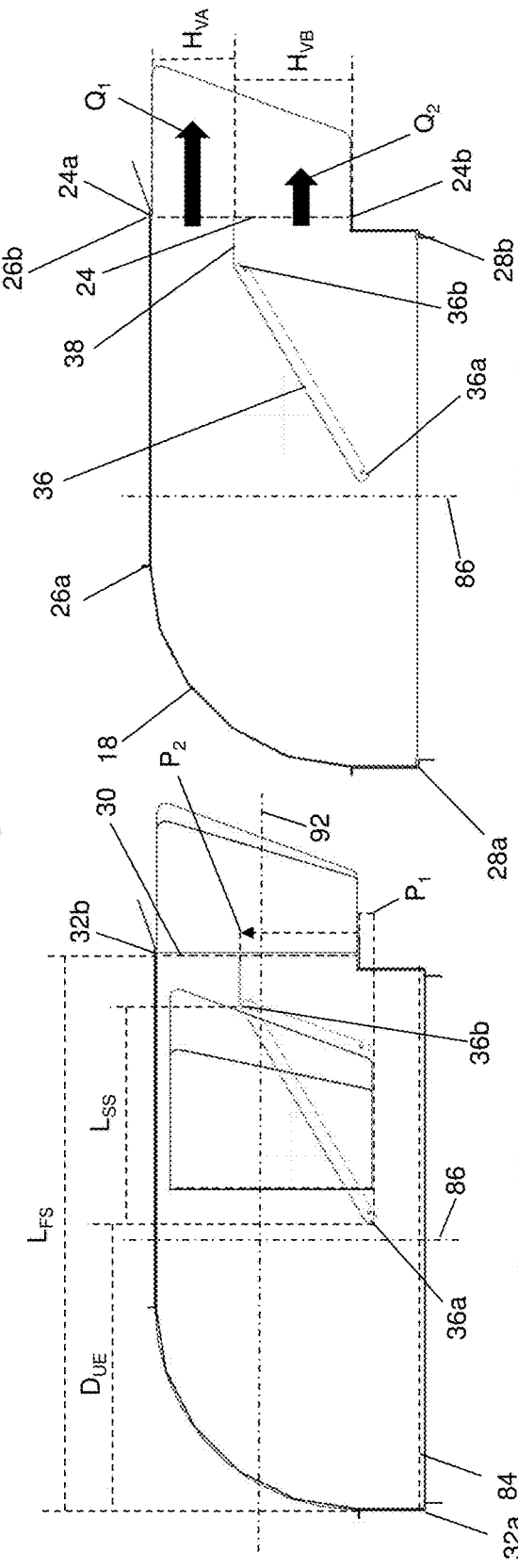

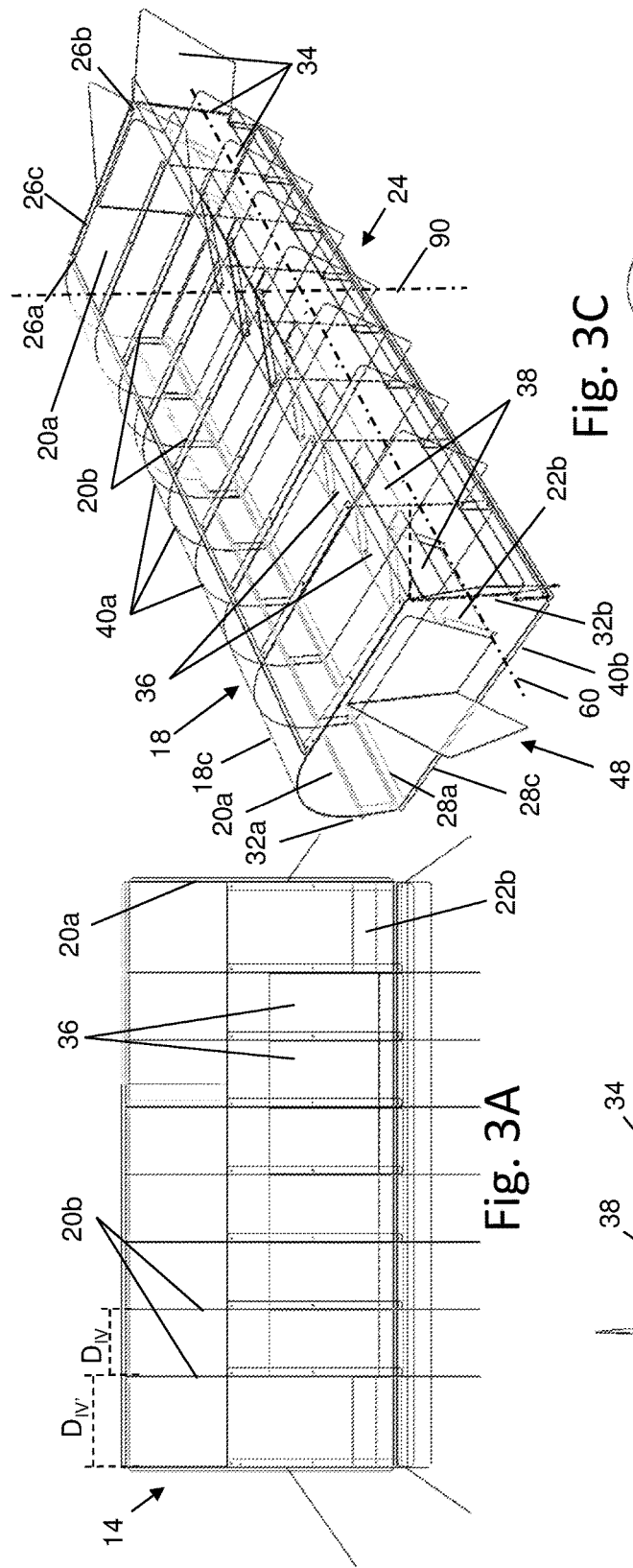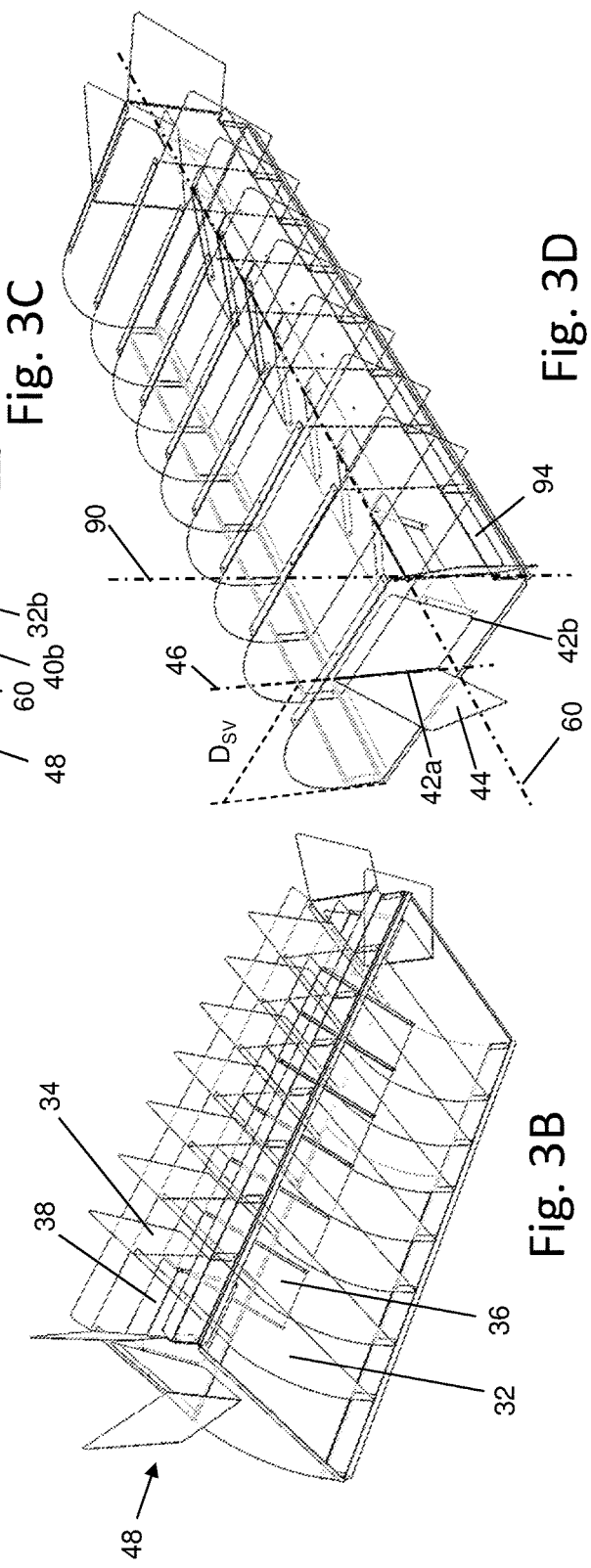

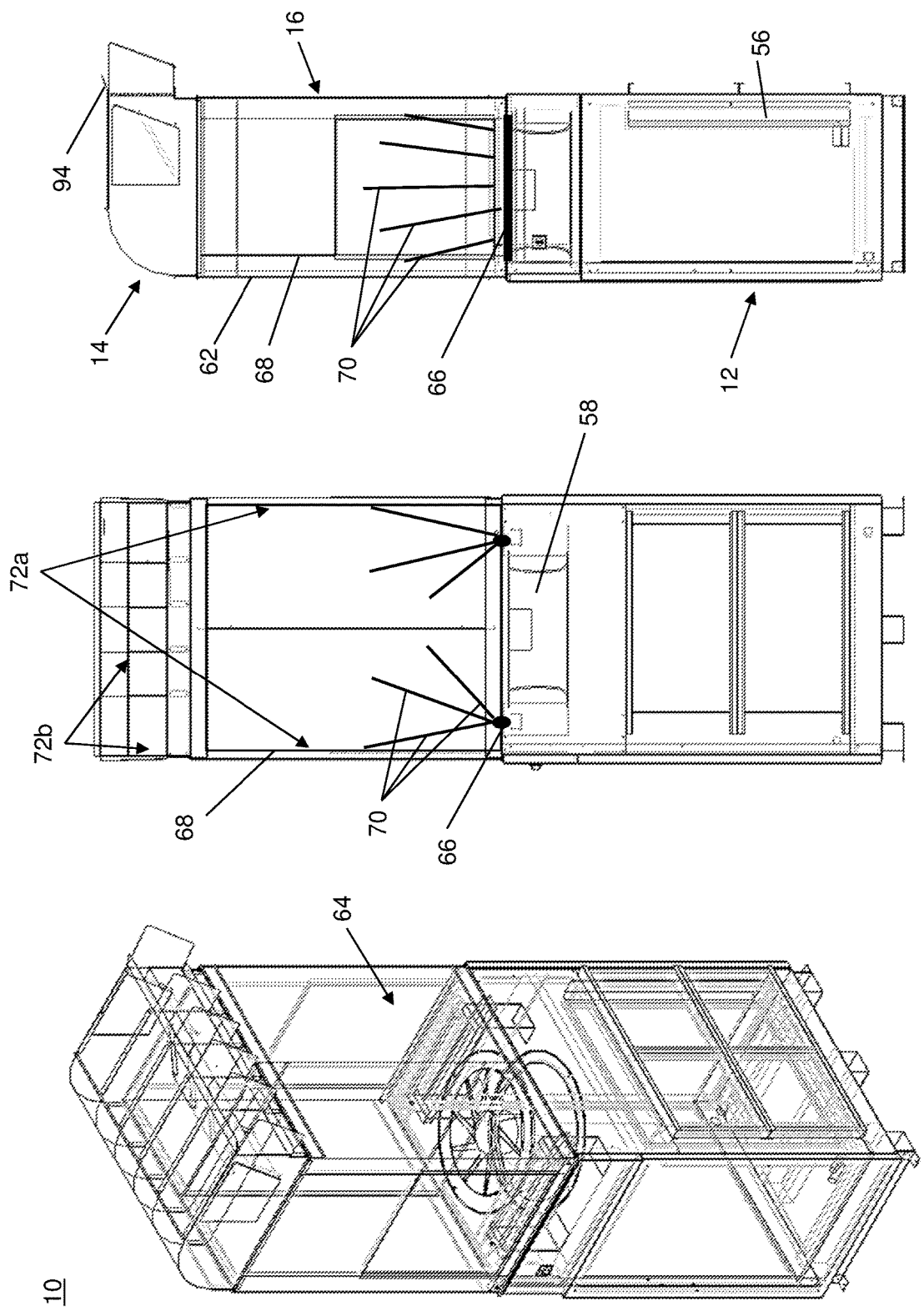

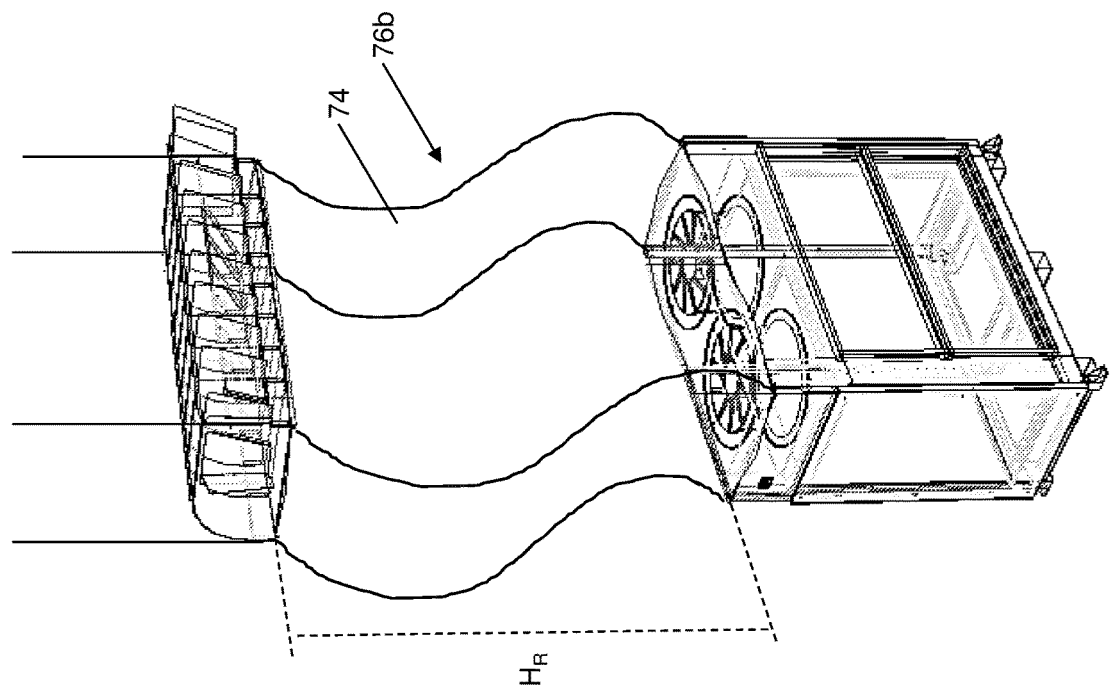
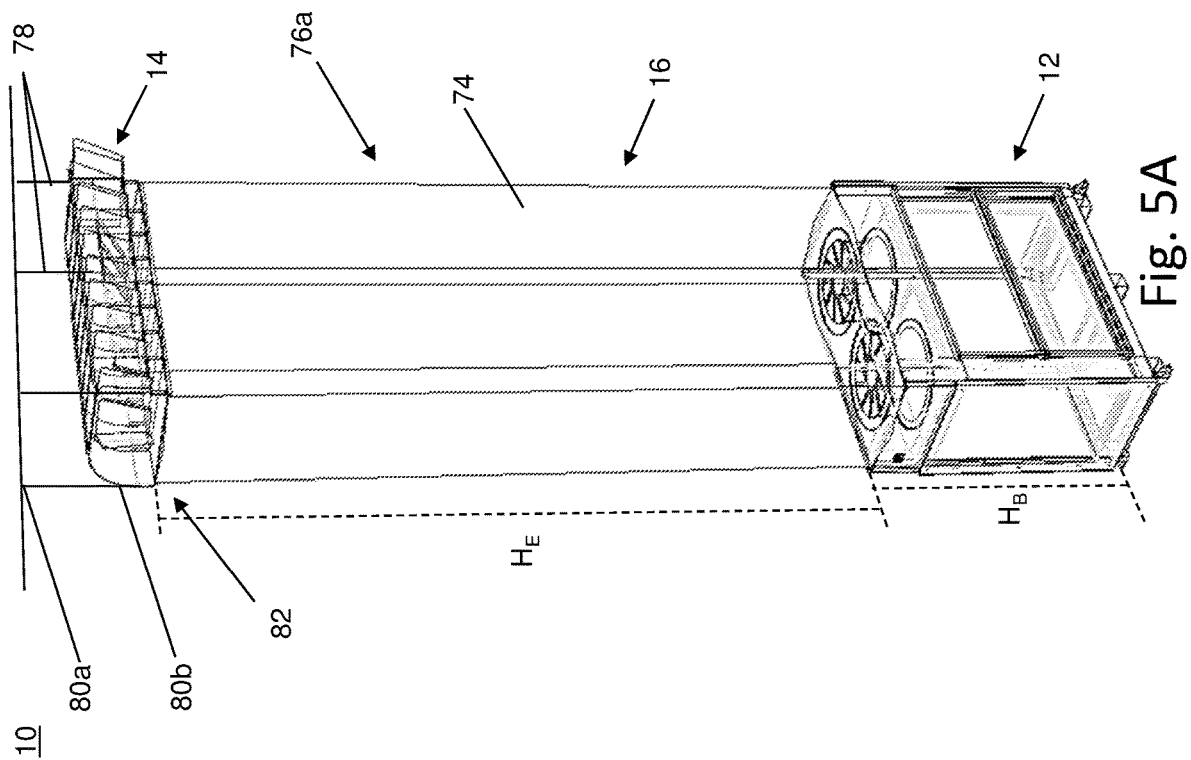

DUCTLESS AIR DISTRIBUTION SYSTEM

CROSS-REFERENCE TO RELATED APPLICATIONS

This application is a continuation-in-part of U.S. patent application Ser. No. 17/150,402 filed on Jan. 15, 2021 which claims priority from U.S. Provisional Pat. App. No. 62/965,474 filed on Jan. 24, 2020, both of which are hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to an air handling system, and more particularly to an air handling system capable of directing airflow into a space without ductwork.

Related Art

Air handling and heating, ventilation and air conditioning (HVAC) systems have long been used for circulating and conditioning air within a given space. In most cases these systems include a rooftop unit (RTU) with or without ductwork, an outdoor ground-mounted unit or an indoor air handler split system which both have field-installed ductwork that distributes conditioned air to certain positions throughout a space. These common systems are generally designed to deliver the lowest upfront equipment cost but often times result in not only higher total installed costs considering required ductwork, cranes, and/or of curbs but also higher operating costs where higher static fans must accompany ductwork. Further, these systems provide mediocre comfort levels due to uneven air distribution. Accordingly, those having a skill in the art seek to reduce or eliminate issues in these common systems by providing an improved air handing system.

For example, although the rooftop unit itself may have a lower production cost and does not require field piping or charging, installation and maintenance requires rooftop access and heavy equipment. Further, rooftop systems are often paired with ductwork within a space and result in poor air circulation and stratification within the space. In addition, ductwork requires higher static fans and the system as a whole produces higher sound levels with decreased overall efficiency.

In other common systems mentioned above, an indoor split system air handler or an outdoor ground-mounted unit may improve on stratification within a space as compared to the RTU and have lower installation costs despite requiring field piping and charging. However, both of these systems are routinely paired with ductwork and thus require corresponding fans, provide less-than-optimal air distribution, offer limited control options where they are limited to indoor air and humidity, have high sound levels, and can result in undesirable aesthetics considering many are fabricated in the field during installation. Accordingly, there is a desire to develop an air system which provides uniform air distribution and de-stratification in an open space, allows for optional outside air intake and humidity control, allows for an optional economizer mode to increase supply airflow, and eliminates the need for field fabrication by providing a completed unit with a clean aesthetic look.

Further, there is a desire to provide an improved system which does not need to integrate with a duct system to effectively distribute air within a space where ductwork necessarily require additional costs, complexities and inefficiencies at the time of installation and throughout the lifetime of the unit. For example, ductwork can require extensive engineering and design considerations in order to properly size and layout mains, branches, and returns in a space. In addition, traditional ducted systems typically require higher-static fans with larger motors and higher energy consumption in order to deliver the same total airflow as a ductless system.

Further still, there is also a desire to integrate an ultraviolet germicidal irradiation system within an air handler that takes advantage of the ultraviolet light proven to eliminate and deactivate airborne pathogens. Although the efficacy in using ultraviolet light to eliminate airborne pathogens is generally known and used in other air handler system, common issues exist given the negative effects of unintended exposure and safety challenges when using ultraviolet light in air handling systems. Accordingly, there remains a desire to those in the art to provide an improved air handling system that safely integrates an ultraviolet germicidal irradiation system while maintaining a high airflow level.

Given the complexity and scope of many designs, upfront material and installation costs are also a drawback in addition to the necessary cleaning and maintenance that are required throughout the life the ductwork. In addition, the restriction of airflow in ductwork necessitates larger or higher-power circulation fans and blowers to overcome the associated air pressure drop which results in more costly fans and ongoing energy costs. Further, the delicate balance of airflow through various registers and diffusers often results in non-uniform distribution of airflow throughout the conditioned space, creating uncomfortable "hot spots" and "cold spots" within the space. Given the many shortcomings of systems that require ductwork, there is a desire to those having a skill in the art to provide an air handling system that does not require ducts while uniformly conditioning air in an open space and thereby reduce installation costs, installation time, energy costs, and air distribution issues that may be associated with ducted systems.

Examples of known air handling units and related systems are described in U.S. Pat. No. 2,984,416 by Nelson B. Johnson, which is hereby incorporated by reference. According to the Johnson '416 Patent, ductless air handlers are particularly suited for use in buildings with large open spaces, such as warehouses and manufacturing facilities. In the air handler, air from the plenum chamber is released through screened outlets directly into the interior of the building, and given the size of the spaces being serviced, merely directing the air outward from one or more units had been sufficient for the satisfactory mixture of the forced air into the ambient air throughout the large space. However, when smaller spaces are being serviced or more control is desired to service a particular area within a larger space, current ductless air handlers may not be suitable for the task. Accordingly, there remains a need for better control of the airflow through the outlets at the top of ductless air handlers. Additionally, the sound level for the industrial ductless air handlers used for warehouses, manufacturing facilities, and other large spaces were typically not important because the sound of the air handler was insignificant compared to the sounds of the machinery, vehicles, and other equipment being put to use in the facilities. For ductless air handlers that a incorporated into smaller spaces, such as retail stores, restaurants, multipurpose rooms and event spaces, and open work spaces, reducing the sound of the air handler may also be an important to the success of the integration of the unit(s) into the space(s).

SUMMARY OF THE INVENTION

The Johnson LITE "Mini" Air Rotation® unit is a ductless air handler having a base which houses a fan, heating and cooling elements and conduit that connects the base to an outlet. The ductless air handling system draws return air, and fresh outside air in some applications, from a low level and discharges conditioned supply air at a high level, thereby de-stratifying and covering a large area without the need for field-installed ductwork. The outlet includes multiple lateral and upright vanes that extend from an upstream end within the outlet proximal to the turning vane on the rear of the unit to a downstream end positioned proximate to the vent of the outlet, preferably beyond the exit plane on the front of the unit. The upright vanes include internal sections within the housing and external louvers that are connected to the internal sections and extend beyond the exit plane. In addition, lateral vanes are situated between each upright vane to divide the airflow into one stream that exits through an upper section of the vent and another stream that exits through a lower section of the vent.

Perforated sections preferably connect the external louvers to the internal sections of the upright vanes, and each external louver can move independently of the other external louvers. Side louvers are also provided on the side upright vanes which open and close to allow airflow not only through the vent along exit plane on the front face of the outlet but also through the two side vents within the side upright vanes of the outlet.

As with other ductless air handlers, an intake is provided in the base portion which houses a fan and may also house an air conditioning element, power element and control element. After air is pulled in through the base via a continuously circulating fan system, the conditioned air travels through the conduit to the outlet of the air handler. As the air reaches the outlet, the air is guided by the upright and lateral vanes and is discharged through the vent into the desired area of the surrounding environment as directed airflow controlled by the independently adjustable louvers and flaps.

The conduit generally connects the base to the outlet and can be made from any number of materials but a particular embodiment of the air handler described herein includes a conduit with a variable height. The variable height conduit is made from a fabric material and can be extended into a taut state when the outlet is suspended above the base by a set of hangers. Conversely, the outlet can be removed or repositioned on a structural support supporting the outlet and the fabric can collapse into a loose state with a reduced height between the base and the outlet. Accordingly, the height between the outlet and the base can be adjusted without necessarily changing the conduit that connects the base to the outlet.

In another alternative embodiment, an ultraviolet (UV) germicidal irradiation chamber can be positioned within the conduit and the air handler can thereby be used to eliminate airborne pathogens within the air that passes through the air handler. The chamber includes a UV lamp and a liner that delivers a UV dosage of having a UVGI Rating Value (URV)-13 or higher, and is typically combined with a MERV-13 pleated filter within the base for additional air purification. Dose depends on exposure time of the air and intensity of the ultraviolet light within the chamber and the extended vertically extending chamber within the conduit enables low-velocity airflow, creating longer exposure to high-intensity ultraviolet light. Additionally, the liner of the chamber is designed with a highly-reflective interior liner to increase ultraviolet intensity throughout while the interior of the outlet and vanes therein are coated in a non-reflective material to prevent leaking of stray ultraviolet light that can be harmful to individuals nearby the air handler.

In another aspect of the air handler described herein, the walls of the base, conduit and outlet may be coated with sound dampening liners to provide a quieter air handler. Further, the upright and lateral vanes within the outlet may also be coated in or made from a sound dampening material to provide an even quieter air handler than those that merely have sound dampening liners on the walls of the air handler.

In another alternative embodiment, the air handler may include an optional feature for fresh outside-air intake. This is accomplished with a bypass damper or a powered air intake to feed air beneath the unit to enable outside air to pass through the same filters and coil as it mixes with return air.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 2A-2C respectively depict detail top, side and side cross-sectional views of the outlet according to the invention described herein.

FIGS. 3A-3D depict detail views of the outlet according to the invention described herein.

FIGS. 4A-4C show an alternative embodiment of the ductless air handling system having an ultraviolet germicidal irradiation chamber according to the invention described herein.

FIGS. 5A-5B show an alternative embodiment of the ductless air handling system having an extendable conduit according to the invention described herein.

DETAILED DESCRIPTION OF THE PREFERRED EMBODIMENTS

The following description of the preferred embodiment(s) is merely exemplary in nature and is in no way intended to limit the invention, its application, or uses.

Figure 1C:
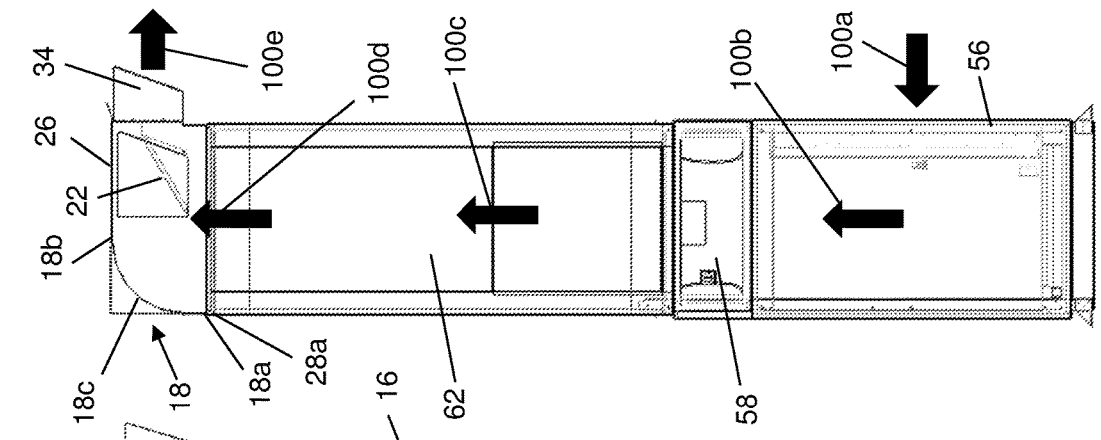
FIGS. 1A-1C respectively depict a perspective, front and side view of the ductless air handling system according to the invention described herein.
Figure 1B:
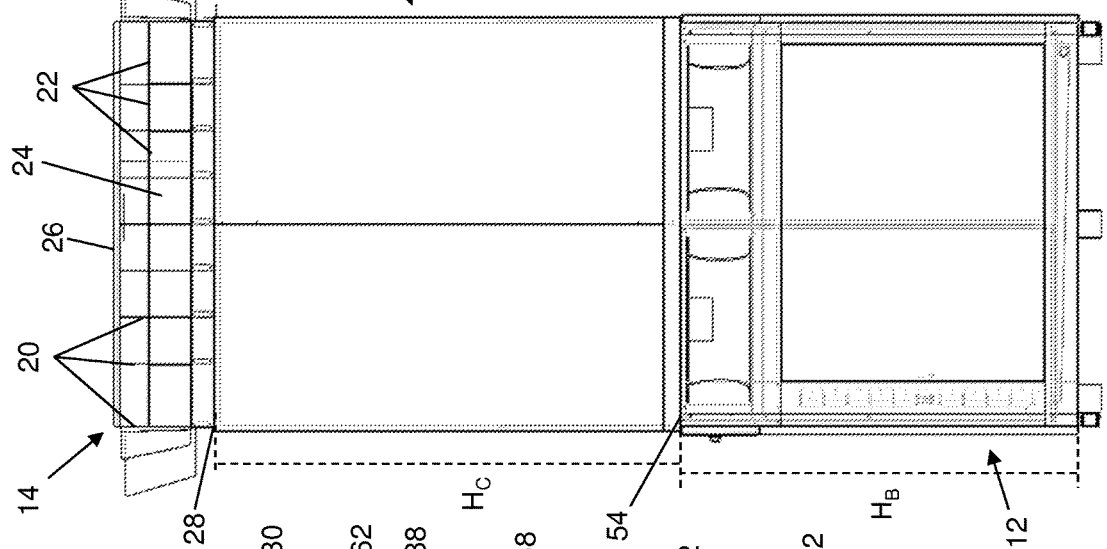
Figure 1A:
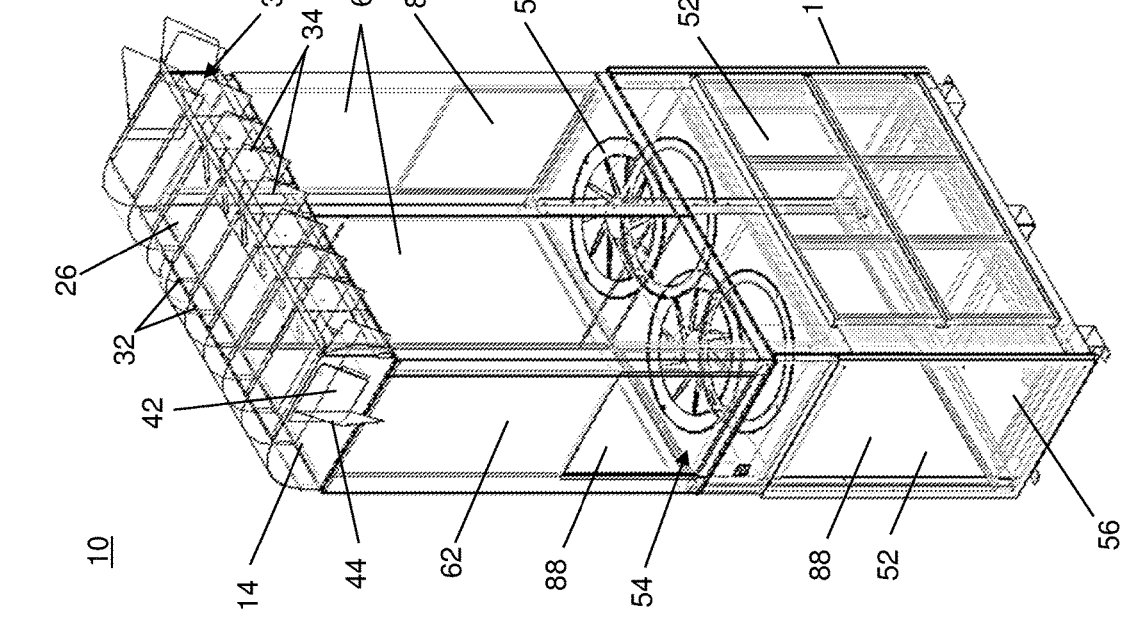

As generally shown in FIGS. 1A, 1B, and 1C, the Johnson LITE Air Rotation® ductless air handler 10 includes a base which houses one of more fans 58 that draw ambient air 100*a* into a plenum of air 100*b* in the air handler conduit that extends between and connects the base to an outlet. High-capacity airflow 100c is provided at 5,000-15,000 cubic feet per minute (CFM) through one or more fans and can be adjusted with changes to fan speed and/or fan quantity depending on the particular need. As particularly shown in FIGS. 1A, 1B, 2A, 5A, and 5B, an air handler with a pair of fans 58 provides 10,000 CFM airflow. It will be appreciated that with another fan in a larger size air handler, the air handler's airflow capacity could be 15,000 CFM; similarly, as discussed below with regard to FIG. 4, a single fan in a smaller handler would be rated at 5,000 CFM airflow. Corresponding with the size of the air handler, its airflow covers a large area with minimal fan power and associated operating, installation and maintenance costs because there are no ducts to install, clean and maintain, and the air handler can simply be installed and powered with a standard 120V outlet. As explained herein, the system uses the Air Rotation® air handler effect to uniformly exchange air throughout space from floor-to-ceiling with high capacity airflow while only taking up a small footprint. Furthermore, the mechanicals within the base are easily accessible at ground level and thereby eliminates the need to go onto the roof of a building as with most other air handler units.

The handler preferably has a vertical orientation to its longitudinal axis with the conduit and outlet positioned above the base so the return air 100a is drawn into the base through the intake at the bottom of the handler and is conditioned 100b, 100c before being discharged as supply air 100e through the vent of the outlet at the top of the handler. As shown in FIGS. 3A-3D and described in detail below, the outlet includes a turning vane on the rear of the outlet and directs the conditioned airflow 100d from the conduit as it enters the outlet towards the vent along an exit plane on the opposite side of the outlet. Multiple upright vanes having an internal section within the outlet and a louver connected to the internal section proximal to the exit plane on the front side of the outlet to direct airflow as it exits through the vent. Further, lateral vanes having scoops situated between each upright vane split airflow into an upper stream and a lower stream that respectively exit through an upper and lower sections of the vent, and adjustable flaps connected to the downstream end of the scoops allow the airflow to be directed upwards or downwards.

The base 12 includes a bottom panel 50, set of sidewalls 52 with an intake 56 positioned on one of the sidewalls and an open topside 54 spaced a base height ($H_B$) from the bottom panel. In operation, the air handler unit described herein is designed to utilize the "Air Rotation" effect to uniformly condition air within an open space as airflow is drawn into the handler through the intake at a low point on one of the sidewalls of the base and discharged at a high point through the outlet positioned above the base. Accordingly, the low-static axial fan 58 is positioned within the base and directs the airflow through the conduit towards the outlet which turns and straightens the air with low air-pressure-drop, while providing adjustable lateral front flaps and upright louvers to enable desired distribution of conditioned air throughout the space in particular directions as further described herein.

In the preferred embodiment, the base also includes various conditioning elements which may include filters, heating elements, cooling elements, power and control elements and a condensate drain. For example, as shown in FIG. 1A, six (6) pleated filters are located in front of the air intake, preferably being secured in slide tracks directly in front of the coil intake. The air handler may also include a washable pre-filter to extend the life of the pleated filters. Return air that enters the handler through one or more filters is thereby conditioned in the base of the handler and subsequently discharged back into the space. In embodiments having a heating and cooling element, the coil is connected to a separate source of chilled water, hot water, or refrigerant flow and may also include a condensing unit, heat pump, or VRF system. Furthermore, although alternative embodiments could house the fan, power, control, heating and cooling elements within the conduit rather than the base, it is preferred that these elements be housed within the base so for easier service with the base being positioned on ground level and so that the conduit can be outfitted with the ultraviolet germicidal irradiation chamber further described herein.

The top of the base subsequently connects to the bottom of the conduit and forces air through the conduit and into the outlet bottom opening connected at the top of the conduit. Accordingly, the conduit 16 extends between the base and outlet and further raises the height of the outlet relative to the base. Although the conduit itself may be made from various lightweight materials, it generally includes sidewalls 62 that extend a height ($H_C$) between the open bottom side of the base and the bottom opening of the outlet. As further explained herein, the airflow entering the outlet through the conduit is subsequently directed by the curved turning vane and the set of upright vanes and the set of lateral vanes and exits the air handler passing through the vent along exit plane or through the side vents in some alternative embodiments described herein.

As particularly shown in FIGS. 2 and 3, the outlet 14 includes a top panel 26, a back panel 18, a set of upright vanes 20 and lateral vanes 22, a vent 24 along an exit plane 30 of the outlet and a bottom opening 28 connected to the conduit. The upright vanes further include a pair of outlet sidewalls 20a and a plurality of internal vanes 20b spaced a distance ($D_{IV}$) from one another between the pair of outlet sidewalls. The back panel 18 preferably spans across the rear section of the upright vanes 40a opposite from the vent and its lower portion 18a and upper portion 18b respectively connects to the top of the conduit's back sidewall and the top panel. Preferably, the back panel is formed as a curved turning vane 18c that extends between the rear edge of the bottom opening 28a and the back section 26a of the top panel. Although the curved turning vane is preferably formed as a part of the back panel in the embodiments as shown in the drawings, it will be appreciated that the back panel could extend straight up to the top panel, and the curved turning vane could be a separate sheet of material within the interior space of the outlet. Additionally, it will be appreciated that the upright vanes do not necessarily need to extend from the lateral vanes back to the back panel and could be coextensive with or longer than the lateral vanes and not contact the back panel.

Opposite from the curved turning vane, the vent extends a vent height ($H_V$) along the exit plane from a top edge 24a connected to front section of the top panel 26b to the bottom edge 24b proximate to the front edge of the bottom opening 28b. To close the sides of the outlet, the pair of outlet sidewalls respectively extend upwards from the side edge of the bottom opening 28c and connect to the respective side sections 26c of the top panel and turning vane 18c. Accordingly, the outlet includes a bottom opening that receives the airflow from the conduit and an open vent along the exit plane opposite from the turning vane.

Each of the upright vanes include an internal section 32 and a louver 34 that connect to one another proximate to the exit plane. Preferably, the internal section is fixed in place and the connection between the internal section and the louver is perforated to allow the louver to be adjustable relative to the fixed internal section. As particularly shown in FIGS. 2 and 3, the internal sections of the upright vanes extend a fixed section length ($L_{FS}$) between a proximal end 32a connected to the curved turning vane and a distal end 32b connected to the corresponding louver proximate to the exit plane. The adjustable louvers extend beyond the exit plane and pivotally connect to the distal ends of the internal section along a substantially vertical axis 90 proximate to the exit plane. Although the preferred embodiment shown in the drawings depicts the adjustable louvers connected to corresponding fixed sections along the exit plane such that the louvers are outside of the outlet and the fixed sections are within the outlet, it will be appreciated that the pivotal connection need only be located proximate to the exit plane to provide sufficient clearance for the louvers to pivot. Additionally, as an alternative to the perforated adjustable connection, a reduced thickness of material could be used at the interface between the fixed section and the louver, i.e., a living hinge, or a fastener could be used when the louver is separate from the fixed section. Thus, the distal ends of the fixed sections may extend beyond the exit plane, outside of the outlet, and conversely portions of the adjustable louvers may be located within the outlet with only a portion extending beyond the exit plane.

In addition, the outlet includes a set of lateral vanes positioned between adjacent fixed sections of corresponding upright vanes. Similar to the upright vanes described herein, each lateral vane includes a fixed scoop section 36 that extends a scooped section length ($L_{SS}$) between an upstream end 36a that is spaced a distance ($D_{UE}$) from the curved turning vane to a downstream end 36b proximate to the distal end of the fixed sections. Although the scoop sections are illustrated as flat panel sections 22a of the lateral vanes, it will be appreciated that they could have an arcuate shape similar to the curved turning vane. To further direct airflow in a particular direction, adjustable front flaps 38 are connected to the downstream end of the scooped sections and pivot along a transverse axis 60 between the adjacent fixed sections of corresponding upright vanes. Similarly, lateral flaps 94 may also be connected along the top and bottom edges of the vent, respectively above and below the adjustable louvers to provide additional airflow direction without interfering with the flaps within the outlet or the louvers. To assure that the lateral vanes do not interfere with the adjustable louvers of the upright vanes, the scooped section lengths are less than the fixed section lengths ($L_{SS}<L_{FS}$), and the adjustable front flaps extend from the downstream end of the scooped sections towards the distal end of the fixed sections but do not extend past the distal end, thereby allowing the louvers and front flaps to pivot without interfering with one another.

The upright and lateral vanes collectively provide the overall form and structure of the outlet to facilitate a simple and intuitive assembly process without the need for specialized equipment and are designed to gently straighten the airflow and provide directional control with the adjustable louvers and front flaps. As discussed herein, the louvers preferably extend beyond the outlet to lengthen the contact area and improve the desired deflection of airflow for directional control while the lateral flaps between the upright vanes allow for upwards and downward deflection of the airflow. Accordingly, the outlet functions to turn airflow with minimal turbulence and air-pressure drop by straightening airflow and providing the ability to adjustable flow direction both vertically and horizontally by the upright louvers and front flaps, respectively. In addition, the exterior skin is lined with a sound-dampening insulation to provide an additional improvement over air handlers in the prior art that are not only noisy but also fail to provide both vertical and horizontal adjustability.

In another aspect of the outlet according to the invention described herein, the exit plane is substantially perpendicular to an entrance plane 84 proximal to the bottom opening of the outlet and the upstream ends of the lateral vanes are located above a bottom side 40b of the upright vanes at a first vertical position ($P_1$) lower than the edges of the vent. As shown in FIGS. 2B and 2C, the upstream ends of the lateral vanes are positioned slightly forward of the midsection 86 in the bottom opening of the outlet to direct a greater volume of airflow above the lateral vane. Further, the vent opening ($H_{VA}$) above the lateral vane is smaller than the vent opening below the lateral vane ($H_{VB}$) given the downstream ends of the lateral vanes and the front flaps are located at a second vertical position ($P_2$) above a halfway height of the vent 92 (i.e., $H_V/2$, where $H_{VA}+H_{VB}=H_V$ and $H_{VA}<H_{VB}$). Accordingly, the greater volume of airflow exiting the vent above the lateral vane ($Q_1$) is accelerated as it is discharged through the vent and projects into the room above the slower airflow exiting the vent below the lateral vane ($Q_2$), i.e., $Q_1>Q_2$.

As explained above, the outlet sidewalls form the sidewalls of the outlet and extend from the proximal end connected to the curved turning vane to the distal end connected to the vent. Each outlet sidewall may also each include a side vent 42 and a side louver 44, as shown in FIGS. 2 and 3. Each side vent includes a rear edge 42a spaced a distance ($D_{SV}$) from the curved turning vane, forward of the upstream end of the fixed scooped sections within the outlet and a front edge 42b proximal to the downstream end of the fixed scooped section. The side louvers connect to the rear edges of the vents and pivot to allow air to be discharged through the side vents of the outlet in addition to the vent along the front exit plane. In operation, the side louver pivotally connects to the outlet sidewall along a substantially vertical axis 46 at the proximal end aligned with the rear edge of the side vent and can be pivoted along the substantially vertical axis into a fully open position 48 with the distal end flared outward from the front edge of the side vent. The side louver can also be closed to prevent airflow from exiting the outlet through the side vent. As with the internal vanes, the outlet sidewalls can also have a louver 34 at the front proximate to the exit plane.

Outlet embodiments that include side vents also include lateral vane scoop sections 22b connected between the outlet sidewalls and the fixed sections of the internal vanes adjacent to the outlet sidewalls that are more vertical than the scoop sections of the plurality of other internal lateral vanes between the internal vertical vane sections. As particularly shown in FIGS. 2B, 3C and 3D, the side scoops are aligned with a front edge of the side vents in the pair of outlet sidewalls and airflow that travels below the lateral scoop cannot exit through the side vent and must exit through the vent along the exit plane beneath the front flap. Furthermore, when side vents are provided and the outlet discharges air from the sides vents as well as through the front vent, it is preferred to space the internal vanes adjacent to the respective outlet sidewalls a distance ($D_{IV'}$) from the outlet sidewall that is greater than the distance from the adjacent internal vane ($D_{IV'}>D_{IV}$) to facilitate greater airflow between these vanes with a greater vent area.

As a large ductless air handler, uniform distribution of conditioned air throughout the space is critical to performance. Accordingly, the innovative outlet assembly described herein provides large surfaces to straighten airflow and reduce turbulence, associated noise and air pressure drop while the large adjustable louvers and flaps provide directional control of conditioned airflow. Thus, a user has even more control on flow direction of supply air out of the vent given they can not only adjust airflow through the exit plane from side to side and up to down by adjusting the upright louver sections and internal lateral flaps respectively, but also can allow air to be discharged through the side vents of the outlet by opening or closing the side louvers.

In another aspect of the air handler shown in FIGS. 4A, 4B, and 4C, the conduit may house an ultraviolet (UV) germicidal irradiation chamber 64 having a liner 68 and an ultraviolet lamp 66. Persons having an ordinary skill in the art will appreciate that UV-C, equating to an ultraviolet light 70 in the range 200-280 nm, has a substantial disinfecting effect on airborne pathogens. Accordingly, the air handler described herein can include an ultraviolet germicidal irradiation chamber within the conduit that produces an ultraviolet irradiance between 790 and 810 $\mu$W/cm$^2$ approximately one meter from the ultraviolet lamp and subsequently delivers an ultraviolet dose of at least 20 J/m$^2$ to the air within the conduit. Nearly all pathogens are susceptible to deactivation from UV-C and the UVGI Rating Value (URV) has established a standardized method of rating an air systems for estimated dose by accounting for exposure time in view of the intensity of UV-C. Accordingly, the system described is designed to meet or exceed the URV-13 rating equating to an ultraviolet dose of 20 J/m$^2$, which can deactivate over 99% of Coronavirus and other airborne pathogens with each pass through the air handler.

Although the amount of ultraviolet irradiation absorbed by an exposed population of microbes is dependent on exposure time and intensity of the UV-C light, the vertical conduit and irradiation chamber positioned therein enables low-velocity airflow that creates longer exposure to high-intensity ultraviolet light. Furthermore, the irradiation chamber is also preferably combined with one or more MERV-13 pleated filters for additional air purification. As with the filters described above for the standard air handler, the filters slide into place on tracks in front of the air handler's intake. Preferably, the intake coil is not used in the intake for the UV germicidal air handler. With a single fan, the air handler can provide 5,000 CFM of continuous air treatment with a single unit being able to treat over 8,000 ft$^2$ depending on desired air change rate in comparison to most off-the-shelf UV air products that have an airflow capacity that is lower by an order of magnitude, providing only a few hundred CFM of airflow.

Although the chamber liner is designed to prevent unwanted ultraviolet light from escaping the conduit as explained below, the liner is coated with a highly-reflective material 72a to increase the intensity of the ultraviolet light throughout chamber. Although the particular type of reflective material is not intended to be limiting, the material itself allows for the air handler embodiment having an ultraviolet germicidal irradiation chamber to exceed a URV-13 rating at while providing 5,000 CFM of continuous air treatment. Further still, the variable airflow allows for the CFM to be dialed down to further increase the UV-C dosage delivered within the irradiation chamber.

A particular challenge in the application of ultraviolet irradiation is safety of nearby persons who may be unintentionally expose to potentially dangerous ultraviolet light. The ultraviolet germicidal irradiation chamber and air handler described herein thereby not only increases the effectiveness of the chamber as described above but also protects against unintentional exposure by enclosing the ultraviolet lamps in the lined chamber that is preferably made of steel and is positioned within the sidewalls of the conduit as shown in FIG. 4. Furthermore, when the ultraviolet germicidal irradiation chamber is used in the air handler, the interior of the outlet and vanes positioned therein are coated in a non-reflective material 72b to prevent leaking of stray ultraviolet light through the outlet and to meet permissible the National Institute for Occupational Safety and Health exposure levels wherein less than 0.2 $\mu$W/cm$^2$ of the ultraviolet light exits the air handler through the outlet and no ultraviolet light otherwise exits the air handler.

Although the conduit according to the present invention is not necessarily limited to one material or structural design, a conduit variation that may be incorporated into the air handler sidewalls made of a fabric material 74 that allows the height and position of the outlet to vary relative to the base. As shown in FIG. 5A, an air handler with fabric sidewalls enables the outlet to be adjusted to different heights given that the fabric can be pulled into a taut state 76a with the conduit having an extended height ($H_E$) or loosened 76b and lowered into to a retracted height ($H_R$) as shown in FIG. 5B. In either state, the conduit still connects the base to the outlet and allows airflow to be drawn into the base at a low level through the intake discharged as supply air through the vent of the outlet above the base. The use of the fabric material for the conduit is particularly beneficial when the extended height of the conduit is greater than twice the height of the base ($H_E > 2*H_B$) to avoid the risk of a top-heavy air handler that could topple because of the increased weight of a relatively tall structural conduit.

In embodiments having a fabric conduit with a variable height, it is preferred that no skeletal support is provided to allow for easier shipment and installation of the handler. Given the conduit preferably has no structural support, these embodiments further include a set of hangers 78, such as but not limited to a cable, that connect to the outlet and suspend the outlet from a structural support, like the ceiling above the handler or cantilevered from a wall proximate to the handler. The hangers include fasteners that connect to the external surface 82 of the outlet on one end 80a and another fastener on the opposite end 80b that can connect to the structural support. Accordingly, the height of the outlet and subsequent tautness of the conduit varies relative to the length of the hangers. In addition, the variable height of the conduit allows some offset from the base where the conduit can extend in any direction around the base, allowing the outlet to be removed from the footprint of the base if desired.

The extendable height air handler with a fabric conduit offers particular advantages over air handlers in the prior art given that they are readily used in taller spaces that require taller air handlers. The fabric conduit inherently overcomes the challenges associated with manufacturing, shipping, installation, and maintenance of larger units without modifying the overall design of the handler. Accordingly, this extendable height conduit can allow the Johnson LITE air handler described herein to be applied to tall spaces while maintaining the core technology described herein. In particular, the standard base section can still house coils, fans, power, controls, filtration, and other systems and the outlet section can still provide smooth transition and ductless distribution of airflow throughout the space as described.

The interconnecting conduit simply needs to deliver air from the base to the outlet and the fabric material allows for easy and inexpensive connections that would necessarily be accomplished with costly custom ductwork or empty filler sections. Multiple conduit sections can also be linked together to be tailor the handler to many height increments given that various length fabric sections can be zippered together to provide desired heights if a single conduit is insufficient. This pre-engineered fabric extension design allows for a quick zipper connection of the fabric sections to the base, one another and the outlet wherein the handler can be installed by positioning the base and hoisting the outlet into the suspended positon wherein it is hung from the roof structure or cantilever from a wall or other structural support. Further still, freight and packaging costs are reduced as the unit can be shipped in a small box with the fabric conduit being folded.

In another alternative embodiment, the air handler may include a high airflow economizer mode for free cooling. The bypass damper may be positioned the backside of the base opposite from the intake and an economizer mode may be activated to draw outside air into the handler when the outside air conditions are cooler and/or drier than the air within the indoor space that would be drawn in through the intake. In operation, the damper draws outside air into the handler in a process known as "free cooling" instead of conditioning indoor air through mechanical cooling. By utilizing the difference in air pressure drop, the system can deliver 125-150% of typical supply airflow when the economizer damper is opened even though the fan speed does not change. In comparison, normal operation has return air airflow of approximately 8,000 CFM into the return whereas outside airflow is 10,000-12,000 CFM through the economizer damper when economizer mode is engaged. In addition, the damper module has total air pressure drop of approximately 0.25 W.C. whereas the return filter and coil have a total air pressure drop of 0.8 W.C.

In another alternative embodiment, the air handler may include an outside air module which combines outside air with the return air for conditioning in the base. To meet most building codes, a minimum percentage of outside air is often required and therefore makes up a small percentage of total airflow. Similar to the bypass damper, an outside air intake module can be provided on the back side of the handler and directs outside air through openings beneath the base to be filtered and conditioned as it blends with return air. Outside air enters the intake module between 1,000-2,000 CFM where small outside air fans are controlled to draw in fresh air during occupied periods. Subsequently, outside air mixes with return air, then passes through filters and coil before exiting the handler through the outlet.

The handler is preferably self-supported by the multiple exterior panels that collectively form the base, conduit and outlet. Accordingly, the unit does not rely on an internal skeletal structure to which the exterior panels connect. However, it will be appreciated that such a unit with a skeletal frame structure could be constructed and function according to the inventive aspects described herein. To reduce noise level of the system during operation, one or more of the external panels can be coated in a sound dampening material. In addition, the vanes may also be coated in a sound dampening material or made there from, such as the internal sections of the upright vanes and the lateral scoop within the outlet. Low turbulence and sound-dampening features also contribute to lower overall sound levels emitted from the system. Further still, the airflow can be adjusted to a lower CFM for extremely quiet operation.

Another benefit is provided in the air handling unit described herein wherein the base comprises approximately 70% of the total weight and provides a low center of gravity to prevent toppling. In addition, the base contains serviceable components, such as but not limited to fans, coils, filters, electrical controls and condensate drainage, which allows for easy ground-level access indoors without the need for unnecessary tools or ladders. To provide an even more manageable unit, the sections are constructed from lightweight insulated sheet metal with lead-ins to facilitate easy and accurate installation and may include access hatches 88 in the sidewalls of the base and the conduit. Lastly, embodiments may include one of a lightweight frame structure that provides attachment locations for foam-injected panels, side panels that can be removed for service access as well as integral forklift pockets for safe and easy handling during installation.

Other elements of the air handler described herein include but are not limited to: outdoor-rated construction materials wherein all sections constructed from durable foam-injected panels; self-contained and integrated refrigeration system that is factory installed which may include energy recovery features from exhaust; heating-only units that include integrated micro-boiler and hydronic system to deliver high-efficiency heating with natural gas or propane; and air structures application that pair unit(s) with various building systems to condition domes, leveraging low sound levels, high efficiency, and slim profile. It will also be appreciated that industrial ductless air handler units, such as described in the Johnson '416 Patent, could be retrofitted with the outlet of the present invention. Additionally, the HVAC elements in the Johnson '416 Patent and other ductless air handler units can be incorporated into the base and conduit of the air described herein.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. For example, the upright vanes described herein include a fixed section and a louver, and there is nothing that would prevent the louver from being actuated. Additionally, the scoop section of the lateral vanes may also allow for adjustments to permit varying flow rates for the upper and lower airstreams that respectively exit from the vent's top portion and bottom portion. Thus, the breadth and scope of the present invention should not be limited by any of the above-described exemplary embodiments, but should be defined only in accordance with the following claims appended hereto and their equivalents.

What is claimed is:

1. An air handler for directing an airflow, comprising:
    a base comprising a bottom panel, a set of base sidewalls, an open topside and an air intake situated along at least one of the base sidewalls, wherein the base houses a fan, and wherein the fan directs the airflow through the air handler;
    an outlet comprising a top panel, a back panel, a vent, a set of upright vanes, a set of lateral vanes, and a bottom opening, wherein the back panel spans across a rear section of the upright vanes and extends between a rear edge of the bottom opening and a back section of the top panel, wherein the vent extends along an exit plane at a front section of the top panel opposite from the back panel, wherein the set of upright vanes are comprised of a pair of outlet sidewalls and a plurality of internal vanes, wherein the pair of outlet sidewalls extend upward from the bottom opening to a corresponding pair of top panel side sections, wherein the internal vanes are spaced a distance from each other between the pair of outlet sidewalls, wherein each of the internal vanes comprises a fixed section and a louver, wherein the fixed sections extend a fixed section length between a proximal end connected to the back panel and a distal end connected to the corresponding louver proximate to the exit plane, wherein each louver extends beyond the exit plane, wherein the lateral vanes are connected between adjacent fixed sections of corresponding internal vanes, wherein each of the lateral vanes has a vane length between an upstream end and a downstream end, wherein the vane length is less than the fixed section length, wherein the upstream end is spaced a distance from the back panel and is positioned more proximate to the bottom opening and the back panel than the downstream end, and wherein the downstream end is positioned more proximate to the vent and the top panel than the upstream end; and a conduit comprising a set of conduit sidewalls extending a height between the open topside of the base and the bottom opening of the outlet, wherein the fan draws the airflow into the air handler through the air intake and forces the airflow to the bottom opening of the outlet through the conduit, wherein the airflow is directed by the set of upright vanes and the set of lateral vanes from the bottom opening to the vent, and wherein the airflow exits the air handler passing through the exit plane of the vent.

2. The air handler of claim 1, wherein the back panel is further comprised of a curved turning vane, wherein the lateral vanes are each comprised of a scoop section and a front flap, wherein the front flap pivotally connects to the scoop section at the downstream end of the lateral vanes and does not extend beyond the distal end of the fixed sections, and wherein the louver pivotally connects to the fixed section.

3. The air handler of claim 2, wherein the front flap pivots about a transverse axis, and wherein the louver pivots about a substantially vertical axis.

4. The air handler of claim 1, wherein the upstream end of the lateral vanes is located at a first vertical position lower than a bottom edge of the vent, and wherein the downstream end of the lateral vanes is located at a second vertical position above a halfway height of the vent, and wherein the upstream end of the lateral vanes is positioned forward of a midsection in the bottom opening of the outlet.

5. The air handler of claim 1, wherein the outlet further comprises a pair of side scoops connected between the outlet sidewalls and the fixed sections of the internal vanes adjacent to the outlet sidewalls.

6. The air handler of claim 5, wherein at least one of the outlet sidewalls further comprises a front louver, a side vent, and a side louver, wherein the front louver is proximate to the exit plane, wherein the side vent comprises a rear edge spaced forward of a midsection in the bottom opening of the outlet and a front edge spaced towards the exit plane of the vent, wherein a proximal end of the side louver pivotally connects to the outlet sidewall at the rear edge of the side vent, and wherein the distal end of the side louver flares outwardly away from the front edge of the vent.

7. The air handler of claim 6, wherein at least one of the side scoops is aligned with the front edge of the side vent.

8. The air handler of claim 1, wherein the conduit further comprises an ultraviolet germicidal irradiation chamber, wherein the chamber comprises an ultraviolet lamp and a liner, wherein the ultraviolet lamp produces an ultraviolet light having a wavelength between 200 and 280 nm, and wherein the ultraviolet germicidal irradiation chamber produces an ultraviolet irradiance between 790 and 810 $\mu W/cm^2$ approximately one meter from the ultraviolet lamp.

9. The air handler of claim 1, wherein the conduit sidewalls are comprised of a fabric material, wherein the fabric material moves between a taut state and a loose state, wherein the height of the conduit varies between an extended height when the fabric material is in the taut state and a retracted height when the fabric material is in the loose state, and wherein the extended height is at least twice a height of the base.

10. The air handler of claim 1, wherein at least a portion of each of the base, the outlet and the conduit are covered in a sound dampening material, and wherein the exit plane is substantially perpendicular to an entrance plane of the bottom opening.

11. An air handler for directing an airflow, comprising:
a base comprising a bottom panel, a set of base sidewalls, an open topside and an air intake situated along at least one of the base sidewalls, wherein the base houses a fan, and wherein the fan directs the airflow through the air handler;

an outlet comprising a top panel, a back panel, a vent, a set of upright vanes, a set of lateral vanes, and a bottom opening, wherein the back panel extends between a rear edge of the bottom opening and a back section of the top panel, wherein the vent extends along an exit plane at a front section of the top panel opposite from the back panel, wherein the set of upright vanes are comprised of a pair of outlet sidewalls and a plurality of internal vanes, wherein the pair of outlet sidewalls extend upward from the bottom opening to a corresponding pair of top panel side sections, wherein the internal vanes are spaced a distance from each other between the pair of outlet sidewalls, wherein the lateral vanes are connected between adjacent internal vanes, wherein each of the lateral vanes has a vane length between an upstream end and a downstream end, wherein the vane length is less than a length of the internal vanes, wherein the upstream end is spaced a distance from the back panel and is located at a first vertical position lower than a bottom edge of the vent, wherein the downstream end is located at a second vertical position above a halfway height of the vent and is positioned more proximate to the vent and the top panel than the upstream end, and wherein the upstream end of the lateral vanes is positioned forward of a midsection in the bottom opening of the outlet; and a conduit comprising a set of conduit sidewalls extending a height between the open topside of the base and the bottom opening of the outlet, wherein the fan draws the airflow into the air handler through the air intake and forces the airflow to the bottom opening of the outlet through the conduit, wherein the airflow is directed by the set of upright vanes and the set of lateral vanes from the bottom opening to the vent, and wherein the airflow exits the air handler passing through the exit plane of the vent.

12. The air handler of claim 11, wherein the back panel is further comprised of a curved turning vane, wherein each of the internal vanes comprises a fixed section and a louver, wherein the fixed sections extend a fixed section length between a proximal end connected to the curved turning vane and a distal end connected to the corresponding louver proximate to the exit plane, and wherein each louver extends beyond the exit plane.

13. The air handler of claim 12, wherein the lateral vanes are each comprised of a scoop section and a front flap, wherein the front flap pivotally connects to the scoop section at the downstream end of the lateral vanes and does not extend beyond the distal end of the fixed sections, and wherein the louver pivotally connects to the fixed section.

14. The air handler of claim 11, wherein the outlet further comprises a pair of side scoops connected between the outlet sidewalls and the fixed sections of the internal vanes adjacent to the outlet sidewalls.

15. The air handler of claim 11, wherein at least one of the outlet sidewalls further comprises a front louver, a side vent, and a side louver, wherein the front louver is proximate to the exit plane, wherein the side vent comprises a rear edge spaced forward of a midsection in the bottom opening of the outlet and a front edge spaced towards the exit plane of the vent, wherein a proximal end of the side louver pivotally connects to the outlet sidewall at the rear edge of the side vent, and wherein the distal end of the side louver flares outwardly away from the front edge of the vent.

16. An air handler for directing an airflow, comprising:
a base comprising a bottom panel, a set of base sidewalls, an open topside and an air intake situated along at least one of the base sidewalls, wherein the base houses a fan, and wherein the fan directs the airflow through the air handler;
an outlet comprising a top panel, a back panel, a vent, a set of upright vanes, a set of lateral vanes, and a bottom opening, wherein the back panel is comprised of a curved turning vane extending between a rear edge of the bottom opening and a back section of the top panel, wherein the vent extends along an exit plane at a front section of the top panel opposite from the back panel, wherein the set of upright vanes are comprised of a pair of outlet sidewalls and a plurality of internal vanes, wherein the pair of outlet sidewalls extend upward from the bottom opening to a corresponding pair of top panel side sections, wherein the internal vanes are spaced a distance from each other between the pair of outlet sidewalls, wherein each of the internal vanes comprises a fixed section and a louver, wherein the fixed sections extend a fixed section length between a distal end connected to the corresponding louver proximate to the exit plane and a proximal end extending back from the exit plane to at least the midsection in the bottom opening of the outlet, wherein each louver extends beyond the exit plane, wherein the lateral vanes are connected between adjacent fixed sections of corresponding internal vanes, wherein each of the lateral vanes has a vane length between an upstream end and a downstream end, wherein the vane length is less than the fixed section length, wherein the upstream end is spaced a distance from the back panel and is positioned more proximate to the bottom opening and the back panel than the downstream end, and wherein the downstream end is positioned more proximate to the vent and the top panel than the upstream end; and
a conduit comprising a set of conduit sidewalls extending a height between the open topside of the base and the bottom opening of the outlet, wherein the fan draws the airflow into the air handler through the air intake and forces the airflow to the bottom opening of the outlet through the conduit, wherein the airflow is directed by the curved turning vane and the set of upright vanes and the set of lateral vanes from the bottom opening to the vent, and wherein the airflow exits the air handler passing through the exit plane of the vent and the side vents.

17. The air handler of claim 16, wherein the lateral vanes are each comprised of a scoop section and a front flap, wherein the front flap pivotally connects to the scoop section at the downstream end of the lateral vanes and does not extend beyond the distal end of the fixed sections, wherein the proximal end for each fixed section of the upright vanes connects with the back panel, and wherein the louver pivotally connects to the fixed section.

18. The air handler of claim 16, wherein the upstream end of the lateral vanes is located at a first vertical position lower than a bottom edge of the vent, and wherein the downstream end of the lateral vanes is located at a second vertical position above a halfway height of the vent, and wherein the upstream end of the lateral vanes is positioned forward of a midsection in the bottom opening of the outlet.

19. The air handler of claim 16, wherein the outlet further comprises a pair of side scoops connected between the outlet sidewalls and the fixed sections of the internal vanes adjacent to the outlet sidewalls.

20. The air handler of claim 19, wherein at least one of outlet sidewalls further comprises a front louver, a side vent, and a side louver, wherein the front louver is proximate to the exit plane, wherein the side vent comprises a rear edge spaced forward of a midsection in the bottom opening of the outlet and a front edge spaced towards the exit plane of the vent, wherein a proximal end of the side louver pivotally connects to the outlet sidewall at the rear edge of the side vent, wherein the distal end of the side louver flares outwardly away from the front edge of the vent, and wherein at least one of the side scoops is aligned with the front edge of the side vent.

* * * * *